US010661078B2

(12) United States Patent
Crosby et al.

(10) Patent No.: US 10,661,078 B2
(45) Date of Patent: *May 26, 2020

(54) MODULAR STIMULATOR FOR TREATMENT OF BACK PAIN, IMPLANTABLE RF ABLATION SYSTEM AND METHODS OF USE

(71) Applicant: MAINSTAY MEDICAL LIMITED, Swords, County Dublin (IE)

(72) Inventors: Peter Andrew Crosby, Blaine, MN (US); Dan Sachs, Minneapolis, MN (US); Prashant Brijmohansingh Rawat, Blaine, MN (US); Jason Alan Shiroff, Edina, MN (US); Johannes Petrus Heemels, Keerbergen (BE)

(73) Assignee: Mainstay Medical Limited, Dublin (IE)

( * ) Notice: Subject to any disclaimer, the term of this patent is extended or adjusted under 35 U.S.C. 154(b) by 367 days.

This patent is subject to a terminal disclaimer.

(21) Appl. No.: 15/853,543

(22) Filed: Dec. 22, 2017

(65) Prior Publication Data
US 2018/0133461 A1 May 17, 2018

Related U.S. Application Data

(63) Continuation of application No. 14/849,478, filed on Sep. 9, 2015, now Pat. No. 9,861,811, which is a (Continued)

(51) Int. Cl.
*A61B 18/14* (2006.01)
*A61N 1/05* (2006.01)
(Continued)

(52) U.S. Cl.
CPC ........ *A61N 1/0551* (2013.01); *A61B 18/1492* (2013.01); *A61N 1/06* (2013.01);
(Continued)

(58) Field of Classification Search
CPC ......... A61B 18/08; A61B 18/10; A61B 18/12; A61B 18/1266; A61B 18/14;
(Continued)

(56) References Cited

U.S. PATENT DOCUMENTS 3,077,884 A 2/1963 Batrow et al.
3,416,534 A 12/1968 Quinn
(Continued)

FOREIGN PATENT DOCUMENTS

CN 1211930 C 7/2005
CN 101678203 3/2010
(Continued)

OTHER PUBLICATIONS

MicroProbes for Life Science, "Nerve Cuff electrodes," available at https://microprobes.com/products/peripheral-electrodes/nerve-cuff, accessed Mar. 5, 2018.
(Continued)

*Primary Examiner* — Michael F Peffley
*Assistant Examiner* — Khadijeh A Vahdat
(74) *Attorney, Agent, or Firm* — Eversheds Sutherland (US) LLP; Christopher C. Bolten; Nicola A. Pisano

(57) ABSTRACT

Apparatus and methods for treating back pain are provided, in which an implantable stimulator is configured to communicate with an external control system, the implantable stimulator providing a neuromuscular electrical stimulation therapy designed to cause muscle contraction to rehabilitate the muscle, restore neural drive and restore spinal stability; the implantable stimulator further including one or more of a number of additional therapeutic modalities, including a module that provides analgesic stimulation; a module that monitors muscle performance and adjusts the muscle stimulation regime; and/or a module that provides longer term pain relief by selectively and repeatedly ablating nerve
(Continued)

fibers. In an alternative embodiment, a standalone implantable RF ablation system is described.

22 Claims, 4 Drawing Sheets

Related U.S. Application Data continuation of application No. 13/045,421, filed on Mar. 10, 2011, now Pat. No. 9,248,278.

(60) Provisional application No. 61/339,957, filed on Mar. 11, 2010.

(51) Int. Cl.
| | | |
|---|---|---|
| *A61N 1/06* | (2006.01) | |
| *A61N 1/36* | (2006.01) | |
| *A61N 1/372* | (2006.01) | |
| A61B 17/00 | (2006.01) | |
| A61B 18/00 | (2006.01) | |
| A61B 18/12 | (2006.01) | |
| A61B 34/20 | (2016.01) | |

(52) U.S. Cl.
CPC ...... *A61N 1/36071* (2013.01); *A61N 1/37211* (2013.01); *A61B 2017/00221* (2013.01); *A61B 2018/00339* (2013.01); *A61B 2018/00577* (2013.01); *A61B 2018/124* (2013.01); *A61B 2018/1467* (2013.01); *A61B 2034/2048* (2016.02); *A61N 1/36042* (2013.01)

(58) Field of Classification Search
CPC ............ A61B 18/1442; A61B 18/1445; A61B 18/1448; A61B 18/1492; A61B 2018/00339; A61B 2018/00577; A61B 2018/124; A61B 2018/1467; A61B 2017/00221; A61B 2034/2048; A61N 1/0551; A61N 1/06; A61N 1/36042; A61N 1/36071; A61N 1/37211
See application file for complete search history.

(56) References Cited

U.S. PATENT DOCUMENTS

| | | |
|---|---|---|
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |
| 3,976,082 A | 8/1976 | Schmitt |
| 3,999,551 A | 12/1976 | Spitz et al. |
| 4,010,757 A | 3/1977 | Jula et al. |
| 4,026,301 A | 5/1977 | Friedman et al. |
| 4,031,899 A | 6/1977 | Renirie |
| 4,149,528 A | 4/1979 | Murphy |
| 4,235,246 A | 11/1980 | Weiss |
| 4,269,198 A | 5/1981 | Stokes |
| 4,342,317 A | 8/1982 | Axelgaard |
| 4,408,609 A | 10/1983 | Axelgaard |
| 4,418,693 A | 12/1983 | Leveen et al. |
| 4,528,984 A | 7/1985 | Morawetz et al. |
| 4,549,556 A | 10/1985 | Tarjan et al. |
| 4,574,806 A | 3/1986 | McCarthy |
| 4,658,835 A | 4/1987 | Pohndorf |
| 4,832,687 A | 5/1989 | Smith, III |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,273,053 A | 12/1993 | Pohndorf |
| 5,300,108 A | 4/1994 | Rebell et al. |
| 5,330,515 A | 7/1994 | Rutecki et al. |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,638,825 A | 6/1997 | Yamazaki et al. |
| 5,733,307 A | 3/1998 | Dinsdale |
| 5,741,321 A | 4/1998 | Brennen |
| 5,782,841 A | 7/1998 | Ritz et al. |
| 5,807,234 A | 9/1998 | Bui et al. |
| 5,873,900 A | 2/1999 | Maurer et al. |
| 5,916,172 A | 6/1999 | Hodges et al. |
| 5,957,968 A | 9/1999 | Belden et al. |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,381,496 B1 | 4/2002 | Meadows et al. |
| 6,406,421 B1 | 6/2002 | Grandjean et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 | 5/2004 | Loeb et al. |
| 6,839,594 B2 | 1/2005 | Cohen et al. |
| 6,845,271 B2 | 1/2005 | Fang et al. |
| 6,862,479 B1 | 3/2005 | Whitehurst et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 | 6/2008 | Rossing et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |
| 7,499,746 B2 | 3/2009 | Buhlmann et al. |
| 7,502,651 B2 | 3/2009 | Kim et al. |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,708,763 B2 | 5/2010 | Selover et al. |
| 7,761,166 B2 | 7/2010 | Giftakis et al. |
| 7,792,591 B2 | 9/2010 | Rooney et al. |
| 7,797,053 B2 | 9/2010 | Atkinson et al. |
| 7,813,803 B2 | 10/2010 | Heruth et al. |
| 7,908,015 B2 | 3/2011 | Lazeroms et al. |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |
| 8,249,701 B2 | 8/2012 | Imran et al. |
| 8,249,713 B2 | 8/2012 | Fang et al. |
| 8,380,318 B2 | 2/2013 | Kishawi et al. |
| 8,386,045 B2 * | 2/2013 | Zhao ................... A61N 1/0551 607/46 |
| 8,391,966 B2 | 3/2013 | Luo et al. |
| 8,409,233 B1 | 4/2013 | Chinn et al. |
| 8,428,728 B2 | 4/2013 | Sachs |

(56) References Cited

U.S. PATENT DOCUMENTS

| | | |
|---|---|---|
| 8,463,383 B2 | 6/2013 | Sakai et al. |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |
| 9,079,019 B2 | 7/2015 | Crosby et al. |
| 9,108,053 B2 | 8/2015 | Crosby et al. |
| 9,320,847 B2 | 4/2016 | Rooney et al. |
| 9,561,364 B2 | 2/2017 | Bondhus |
| 9,861,811 B2 | 1/2018 | Crosby et al. |
| 9,950,159 B2 | 4/2018 | Beck et al. |
| 2001/0053885 A1 | 12/2001 | Gielen et al. |
| 2002/0065543 A1 | 5/2002 | Gomperz et al. |
| 2002/0099419 A1 | 7/2002 | Cohen et al. |
| 2002/0115945 A1 | 8/2002 | Herman et al. |
| 2002/0147485 A1 | 10/2002 | Mamo et al. |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120328 A1 | 6/2003 | Jenkins et al. |
| 2003/0199938 A1 | 10/2003 | Smits et al. |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2006/0004429 A1 | 1/2006 | Mrva et al. |
| 2006/0009810 A1 | 1/2006 | Mann et al. |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2006/0293662 A1 | 12/2006 | Boyer et al. |
| 2007/0027501 A1* | 2/2007 | Jensen ............... A61N 1/3605 607/45 |
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2007/0239224 A1 | 10/2007 | Bennett et al. |
| 2007/0276453 A1* | 11/2007 | Hill ............... A61N 1/36114 607/62 |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0020764 A1 | 1/2009 | Anderson et al. |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2010/0331883 A1* | 12/2010 | Schmitz ............ A61B 17/0218 606/249 |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0190786 A1 | 8/2011 | Gerber et al. |
| 2011/0224665 A1 | 9/2011 | Crosby et al. |
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0218247 A1 | 8/2013 | Sachs |
| 2013/0238066 A1 | 9/2013 | Boggs et al. |

(56) References Cited

U.S. PATENT DOCUMENTS

| | | |
|---|---|---|
| 2013/0245715 A1 | 9/2013 | Peterson |
| 2013/0261696 A1 | 10/2013 | Thacker et al. |
| 2013/0296966 A1 | 11/2013 | Wongsanipigoon et al. |
| 2013/0310901 A1 | 11/2013 | Perryman et al. |
| 2013/0338730 A1 | 12/2013 | Shiroff et al. |
| 2014/0031837 A1 | 1/2014 | Perryman et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0463998 | 2/2014 | Sachs |
| 2014/0114385 A1 | 4/2014 | Nijhuis et al. |
| 2014/0288616 A1 | 9/2014 | Rawat et al. |
| 2014/0350653 A1 | 11/2014 | Shiroff et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |
| 2017/0100408 A1 | 4/2017 | Bertolini et al. |

FOREIGN PATENT DOCUMENTS

| | | |
|---|---|---|
| EP | 0 587 269 A2 | 3/1994 |
| EP | 0 587 269 B1 | 12/1998 |
| EP | 1 053 762 B1 | 11/2000 |
| EP | 1 255 583 A1 | 11/2002 |
| EP | 2 273 931 A1 | 1/2011 |
| WO | WO-01/58520 A1 | 8/2001 |
| WO | WO-2004/066820 A2 | 8/2004 |
| WO | WO-2006/091611 A1 | 8/2006 |
| WO | WO-2006/133445 A2 | 12/2006 |
| WO | WO-2006/135791 A2 | 12/2006 |
| WO | WO-2007/051146 A1 | 5/2007 |
| WO | WO-2007/138598 A2 | 12/2007 |
| WO | WO-2008/048471 A2 | 4/2008 |
| WO | WO-2008/070807 A2 | 6/2008 |
| WO | WO-2008/094952 A2 | 8/2008 |
| WO | WO-2008/112178 A1 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 A1 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 A1 | 2/2013 |
| WO | WO-2013/036630 A1 | 3/2013 |
| WO | WO-2013/096260 A1 | 6/2013 |
| WO | WO-2013/155117 A1 | 10/2013 |
| WO | WO-2014/099423 A1 | 6/2014 |
| WO | WO-2015/059570 A1 | 4/2015 |
| WO | WO-2015/187426 A1 | 12/2015 |
| WO | WO-2018/007914 A1 | 1/2018 |

OTHER PUBLICATIONS

Unit III—The Spine, "Motions of the Spine," available at https://courses.vcu.edu/DANC291-003/unit_3.htm, accessed Mar. 5, 2018.
Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl. 2 (2006):S192-300. http://www.ncbi.nlm.nih.gov/pubmed/16550448.
Baker et al., "Clinical Uses of Neuromuscular Electrical Stimulation," NeuroMuscular Electrical Stimulation—A Practical Guide, 4th ed. Rancho Los Amigos Research and Education Institute Inc., pp. 47-66 (2000).
Bhadra et al., "Peripheral nerve stimulation for restoration of motor function," Journal of Clinical Neurophysiology: Official Publication of the American Electroencephalographic Society, 14(5):378-33 (Sep. 1997).
Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).
Bowman et al., "Effects of Waveform Parameters on Comfort during Transcutaneous Neuromuscular Electrical Stimulation," Annals of Biomedical Engineering, 13:59-74 (1985).
Bradford et al., "Surface Electrical Stimulation in the Treatment of Idiopathic Scoliosis: Preliminary Results in 30 Patients," Spine, 8(7):757-764 (1983).
Brazier et al., "A Comparison of the EQ-5D and SF-6D Across Seven Patient Groups," Health Economics, 13:873-884 (2004).
Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.
Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.n1m.nih.gov/pubmed/22256103.
Crago et al., "The choice of pulse duration for chronic electrical stimulation via surface, nerve, and intramuscular electrodes," Annals of Biomedical Engineering, 2(3):252-264 (1974).
Criterion Inc., "NMES Treatment Protocols," 3 pages (accessed Jun. 7, 2012) available at http://www.criterionmed.com/PDF/NMES%20Treatment%20Protocols.pdf.
Deckers, et al., Chronic Low Back Pain: Restoration of Dynamic Stability, Neuromodulation, 18:478-486 (2015).
Durham et al., "Surface Electrical Stimulation Versus Brace in Treatment of Idiopathic Scoliosis," Spine, 15(9):888-891 (1990).
EMPI, "Low Back Syndrome/Chronic Low Back Pain," NMES Guidelines for Treatment, 2 pages (2003).
Extended European Search Report dated Mar. 5, 2015 in EP Patent Appl. Serial No. 14189412.1
Extended European Search Report dated Jan. 7, 2013 in European Patent Application No. 12176863.
Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.
Freeman, et al., The Role of the Lumbar Multifidus in Chronic Low Back Pain: A Review, American Academy of Physical Medicine and Rehabilitation, 2:142-146 (2010).
Friedman et al., "Electrical stimulation for scoliosis," American Family Physician, 25(4):155-160 (1982) available at: http://www.ncbi.n 1 m.nih.gov/pubmed/6978055 (Accessed Oct. 19, 2011).
Garmirian, et al., Discriminating Neurogenic from Myopathic Disease via Measurement of Muscle Anisotrophy, Muscle Nerve, 39(1):16-24 (2009) (Abstract only).
Gazelle et al., "Tumor Ablation with radio-frequency Energy," Radiology, (2000), 217(3):633-646.
Glaser et al., "Electrical Muscle Stimulation as an Adjunct to Exercise Therapy in the Treatment of Nonacute Low Back Pain: A Randomized Trial," The Journal of Pain, 2(5):295-300 (2001).
Gondin, et al., Electromyostimulation training effects on neural drive and muscle architecture, Med. Sci. Sports. Exerc., 37(8):1291-9 (2005).
Gorman et al., "The effect of stimulus parameters on the recruitment characteristics of direct nerve stimulation," IEEE Transactions on Bio-medical Engineering, 30(7):407-414 (1983).
Haemmerich et al., "Thermal Tumor Ablation: Devices, Clinical Applications and Future Directions," Int. J. Hyperthermia, (2005) 21(8):775-760 (Abstract).

(56) References Cited

OTHER PUBLICATIONS

Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following intervetebral disc lesion," Progress in Motor Control Vi—Brazil. 36:2-3 (2007).
Hodges, et al., Intervetebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
International Search Report & Written Opinion dated Jan. 19, 2016 in Int'l PCT Patent Appl. Serial No. PCT/IB2015/055926.
International Search Report & Written Opinion dated Mar. 19, 2015 in Int'l PCT Patent Appl. Serial No. PCT/IB2014/002920.
International Search Report & Written Opinion dated Apr. 5, 2013 in Int'l PCT Patent Appl. Serial No. PCT/US2012/070259.
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
International Search Report & Written Opinion dated Jun. 25, 2008 in Int'l PCT Patent Appl. No. PCT/US08/03126.
International Search Report and Written Opinion dated Jan. 26, 2016 in Int'l PCT Patent Appl. Serial No. PCT/IB2015/057838.
International Search Report and Written Opinion dated Oct. 16, 2015 in Int'l PCT Patent Appl. Serial No. PCT/US2015/032732.
International Search Report dated Oct. 19, 2011 in Int'l PCT Patent Appl. Serial No. PCT/US2011/027934.
Keller, et al., Muscular Contributions to Dynamic Dorsoventral Lumber Spine Stiffness, Eur. Spine J., 16(2):245-54 (2007).
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Medtronic Extension Passer 3555 Accessory Kit—Technical Instructions, 2 pages (2001).
Medtronic Interstim Therapy 3093 & 3889—Implant Manual, 38 pages (2010).
Medtronic Model 3464 Receiver/Extension Internalization Manual, SE-4 for Spinal Cord Stimulation (SCS), 7 pages (1986).
Miyatani, et al., Validity of Estimating Limb Muscle Volume by Bioelectrical Impedance, J. Appl. Physiol., 91:386-394 (2001).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
OAAO Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/I0.IIII/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent Appl Serial No. PCT/US2015/032732.
PCT International Search Report and Written Opinion dated Sep. 3, 2013 in related PCT Application No. PCT/US2013/045223.
PCT Written Opinion dated Aug. 23, 2013 in Int'l PCT Application No. PCT/US2010/049148.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/articleviewer.aspx?year=1997&issue=00930&article=00002&type=abstract.
Rosatelli, et al., Three-dimensional study of the musculotendinous architecture of lumbar multifidus and its functional implications, Clinical Anatomy 21(6):539-44 (2008).
RS Medical, "RS-4M Muscle Stimulator," available at http://wwv.rsmedical.com/documents/fact_sheet_RS4rn/pdf (last visited Jul. 19, 2012).
Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Sippl, Charles J., "Computer Dictionary: Third Edition," pp. 2257 and 340 (1984).
Sluijter, "Radiofrequency Ablation in the Management of Spinal Pain," C212, (2006), IV(1):10-15.
Solomonow et al., "The Ligamento-Muscular Stabilizing System of the Spine," Spine, (1998), 23(23):2552-2562.
Spinal Fusion Guidelines, MD Guidelines, 2009. www.mdguidelines.com/spinal-fusion.

(56) References Cited

OTHER PUBLICATIONS

Stokes, et al., "Surface EMG Electrodes Do Not Accurately Record from Lumbar Multifidus Muscles," Clin. Biomech, (2003), 18(1):9-13 (Abstract Only).

Van Dieen, et al., "Trunk Muscle Recruitment Patterns," Spine, (2003), 28(8):834-841 (Abstract Only).

Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.

Van Zundert et al., "Radiofrequency treatment for chronic pain syndromes," CPD Anaesthesis, 6(1):13-17 (2004).

Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.

Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAl&dq=Application of Muscle/Nerve Stimulation in Health and Disease&ots=CMV5rXiDQD&sig=Wg8u1YOC4PgvVDzcjdwBub5U2To (Accessed Jun. 2, 2011).

Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.

Ward et al., "Architectural analysis and intraoperative measurements demonstrate the unique design of the multifidus for lumbar spine stability," J. Bone Joint Surg. [Am.] 91:176-185, PMC2663324 (2009).

Wikipedia, "Interference Fit," http://en.wikipedia.org/wiki/Interference_fit, accessed Dec. 4, 2014.

Wikipedia, "Time-division multiplexing," https://en.wikipedia.org/wiki/Time-division_multiplexing (accessed Nov. 12, 2015).

Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).

Written Opinion dated Feb. 3, 2014 in Int'l PCT Patent Appl. Serial No. PCT/US2012/070259.

Written Opinion dated Nov. 16, 2011 in Int'l PCT Patent Appl. Serial No. PCT/US2011/027934.

Medtronic, Kinetra, Soletra, and Itrel II, 8870, Neurostimulators for Deep Brain Stimulation (DBS), Software Application Card, Programming Guide for Software A, Dec. 1, 2003, Published 2005, Retrieved from the Internet: URL: http:://www.boala-parkinson.ro/Carti%20tehnice/dbs-prog8870-gd.pdf [retrieved Aug. 23, 2018].

Medtronic Tunneling Rod Accessory Kit 8590-41—Technical Manual, 9 pages (Sep. 23, 2014).

* cited by examiner

MODULAR STIMULATOR FOR TREATMENT OF BACK PAIN, IMPLANTABLE RF ABLATION SYSTEM AND METHODS OF USE

I. REFERENCE TO RELATED APPLICATIONS

This application is a continuation application of U.S. application Ser. No. 14/849,478, filed Sep. 9, 2015, now U.S. Pat. No. 9,861,811, which is a continuation application of U.S. application Ser. No. 13/045,421, filed Mar. 10, 2011, now U.S. Pat. No. 9,248,278, which claims the benefit of priority of U.S. provisional application Ser. No. 61/339,957, filed Mar. 11, 2010, the entire contents of each of which are incorporated herein by reference in their entireties.

II. FIELD OF THE INVENTION

This application relates to apparatus and methods for treating back pain by combining circuitry for providing neuro-muscular electrical stimulation (NMES) therapy with circuitry for providing analgesic stimulation, performance monitoring and feedback, and/or selective ablation.

III. BACKGROUND OF THE INVENTION

The human back is a complicated structure including bones, muscles, ligaments, tendons, nerves and other structures. The spinal column consists of interleaved vertebral bodies and intervertebral discs. These joints are capable of motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Muscles provide mechanical stability to the spinal column. Cross sectional images of the spine demonstrate that the total area of the cross sections of the muscles surrounding the spinal column is much larger than the spinal column itself. Additionally, the muscles have much larger lever arms than those of the intervertebral disc and ligaments. The motor control system sends signals down nerves to activate the muscles of the back in concert to maintain spine stability.

The multifidus is the largest and most medial of the lumbar back muscles. It consists of a repeating series of fascicles which stem from the laminae and spinous processes of the vertebrae, and exhibit a substantially similar pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles which attach to the mamillary processes attach to the capsules of the facet joints next to the mamillary processes. All the fasicles arriving from the spinous process of a given vertebra are innervated by the medial branch of the dorsal ramus that issues from below that vertebra.

Normally, load transmission in the spinal column is painless, with the muscles acting in concert with the ligaments and bones preventing excessive relative movements of the structures. The neutral zone is the range of intervertebral motion, measured from a neutral position, within which the spinal motion is produced with a minimal internal resistance. Over time, dysfunction of the spinal stabilization system can lead to instability and abnormal movement of the spine, resulting in overloading of structures when the spine moves beyond its neutral zone. High loads can lead to inflammation, disc degeneration, ligament damage, facet joint degeneration, and muscle fatigue, all of which can result in pain.

For patients believed to have back pain due to instability, clinicians first offer a group of therapies that attempts to minimize the abnormal range of motion that leads to the pain. If this group of therapies does not work, then the next group of therapies aims to block the pain produced by the abnormal range of motion.

Common conservative methods of attempting to reduce abnormal motion aim to improve muscle strength and control and include core abdominal exercises, use of a stability ball, and Pilates. If conservative methods of preventing abnormal movement are ineffective, surgical approaches may be used.

Spinal fusion is the standard surgical treatment for chronic back pain. One or more vertebrae are surgically fused together to prevent relative motion. Following fusion, motion is reduced across the vertebral motion segment. Dynamic stabilization implants are intended to reduce abnormal motion and load transmission of a spinal motion segment, without fusion. Total disc replacement and artificial nucleus prostheses also aim to improve spine stability and load transmission while preserving motion.

If pain persists after physical therapy or surgical intervention to prevent the abnormal motion that leads to pain, few options are available for relief.

One option is a technique referred to as "RF rhizotomy", in which radio frequency ("RF") energy is used to ablate the medial branch of the dorsal ramus that contains the afferent fibers responsible for transmitting pain signals from the facet joint. There are several devices available for performing this treatment, such as those offered by Baylis Medical Inc. (Montreal, Canada). While this technique can be effective, it provides only short term relief as nerve fibers may regenerate over time, and generally the procedure must be repeated approximately every six months to maintain effective pain control. The electrical parameters for RF ablation of nerves differ amongst various suppliers.

Another option for pain relief is Transcutaneous Electrical Nerve Stimulation (TENS). This technology provides low energy electrical signals delivered via externally applied skin pad electrodes. While the exact mechanism of action is still subject to some controversy, it is generally believed that the electrical energy blocks the signals in the afferent nerve fibers that transmit the pain signals to the brain.

A modification to this approach is to use percutaneous wires connected to electrodes placed nearer to the nerves (PENS or Percutaneous Electrical Nerve Stimulation). A wide variety of PENS or TENS stimulation parameters have been published, including high-frequency (HF; >10 Hz), low-frequency (LF; <10 Hz), variable-frequency (VF) and acupuncture-like (AL), which employs very low-frequency, high-amplitude stimulation. The intensity of the TENS or PENS stimulation (voltage or current) is generally adjusted to a level which achieves analgesia without causing irritation or pain from the stimulation itself. One such PENS device is described in U.S. Pat. No. 6,671,557.

Implantable devices for electrical stimulation of peripheral nerves for control of pain have been described. For example, U.S. Pat. No. 7,324,852 B2 describes an implantable electrical stimulation device with a plurality of electrodes that are implanted subcutaneously and are stimulated in a pre-determined pattern to provide pain relief.

A Spinal Cord Stimulator (SCS) is an implanted electrical stimulation device with one or more electrodes that are placed adjacent or near to the spinal cord, with the goal of blocking the pain signals from being transmitted via the spinal cord to the brain. Although SCS was originally designed and approved for radicular pain (sciatica), the technique is increasingly being used for lower back pain. Spinal cord stimulators may be self-powered (i.e., contain a primary battery or cell) or may include a rechargeable battery (i.e., a secondary battery or cell), as described for example, in U.S. Pat. No. 6,516,227.

The key drawback with all of the previously known electrical stimulation techniques that seek to block the pain signals (TENS, PENS, SCS and RF Ablation of the nerves) is that relief, if obtained, is usually only temporary, and repeated or continuous therapies are needed.

U.S. Patent Application Publication No. US2008/0228241 to Sachs, assigned to the assignee of the present invention, describes an implanted electrical stimulation device that is designed to restore neural drive and rehabilitate the multifidus muscle. Rather than masking pain signals while the patient's spinal stability potentially undergoes further deterioration, the stimulator system described in that application is designed to reduce the propensity for instability of the spinal column, which in turn is expected to reduce persistent or recurrent pain.

While the stimulator system described in the Sachs application seeks to rehabilitate the multifidus and restore neural drive, it does not provide relief of the pain during the application of the therapy. Thus, it is possible that for some patients the effectiveness of the therapy may be hindered by the continuation of pain, which may interfere with restoration of neural drive to the muscle or impede the patient's ability to tolerate the therapy. In addition, it is possible that as the tone of the multifidus muscle improves during use of the stimulator system described in the Sachs application, it may be desirable to reduce the stimulus amplitude, frequency or duration, or stimulation intervals.

In view of the foregoing, it would be desirable to augment the stimulator system described in the Sachs application with additional therapeutic modalities, such as the ability to alleviate pain during and between muscle stimulation. It therefore may be desirable to provide pain blocking stimulation to afferent nerve fibers simultaneously with muscle stimulation pulses, or at other times.

It further may be desirable, depending upon the severity of the pain experienced by a patient and the degree to which it interferes with rehabilitation of the multifidus muscle, to provide pain blocking by selectively ablating afferent nerve fibers in conjunction with the stimulation therapy described in the Sachs application.

It also would be desirable to combine the rehabilitative stimulation therapy described in Sachs with a capability to monitor muscle performance during the stimulation therapy, and to adjust the applied stimulation pulses to account for changes in the muscle tone and neural drive. In addition, it would be desirable to detect the duration, frequency and strength of muscle contractions to further reduce the patient's perception of pain resulting from the muscle stimulation therapy, for example, to avoid spasm.

IV. SUMMARY OF THE INVENTION

In view of the drawbacks of previously-known methods and apparatus for treating back pain, the stimulator system of the present invention provides a neuromuscular electrical stimulation system designed to rehabilitate spinal stability and restore neural drive, while providing additional therapeutic modalities, such as the ability to alleviate pain during and between muscle stimulation intervals. In accordance with the principles of the present invention, an implantable neuromuscular electrical stimulation system is provided that includes one or more of a number of additional therapeutic modalities: a module that provided analgesic stimulation; a module that monitors muscle performance and adjusts the muscle stimulation regime; and/or a module that provides longer term pain relief by selectively and if necessary repeatedly ablating afferent nerve fibers.

Accordingly, one embodiment of the stimulator system of the present invention combines circuitry to stimulate and rehabilitate the multifidus muscle with circuitry to stimulate afferent nerves to alleviate back pain during and between muscle stimulation intervals. The analgesic pulse regime may be applied to afferent nerve fibers simultaneously with muscle stimulation pulses, or at other times.

In an alternative embodiment, circuitry to stimulate and rehabilitate the multifidus muscle may be combined with circuitry that achieves pain blocking by selectively and repeatedly ablating afferent nerve fibers.

In still another embodiment, circuitry to stimulate and rehabilitate the multifidus muscle may be combined with circuitry to monitor muscle performance during the stimulation therapy, and to adjust the applied stimulation pulses to account for changes in the muscle tone and neural drive. For example, such performance feedback circuitry may detect the duration, frequency and strength of muscle contractions to further reduce the patient's perception of pain resulting from the muscle stimulation therapy, for example, to avoid spasm.

It should be appreciated that while the foregoing additional modalities are described in the context of a neuromuscular electrical stimulation system, such as described in the foregoing Sachs application, such modules may be packaged separately or in other combinations for applications other than treating back pain. For example, the RF ablation module may be implemented as a standalone implantable system for selectively ablating unresectable tumors located in the liver, brain, thyroid, pancreas, kidney, lung, breast, or other body structures, thereby avoiding the need for repeated reoperations. Alternatively, the RF ablation module may be combined with the analgesic stimulation module, such that the analgesic module provides continual pain relief while the RF ablation module provides intermittent ablation of selected afferent nerve fibers or tissue. As an additional example, the analgesic stimulator module may be combined with the performance feedback module, to provide an implantable stimulator that monitors muscle exertion and may adjust the stimulatory regime applied to the afferent nerves to maintain patient comfort.

The implantable electrical stimulation system of the present invention includes an implantable housing connected to at least one or more electrodes placed in appropriate anatomical locations and connected by leads to the housing. Feedthroughs (preferably hermetically sealed) connect the leads to the internal electronic circuitry. Stimulation electrodes may be logically connected in pairs to a stimulation channel designed to supply the stimulation regime needed for the therapeutic modality chosen for that electrode pair. The stimulator system may be arranged so that a different therapeutic modality may be applied to selected electrode pairs simultaneously. For example, the stimulator may apply neuromuscular electrical stimulation to the medial branch of the dorsal ramus to effect contraction and rehabilitation of the multifidus muscle, while simultaneously applying electrical stimulation to a different arrangement of electrodes placed adjacent to the spinal cord to effect spinal cord stimulation to relieve pain.

In general, the stimulator system includes an implantable housing including a controller, a memory, a power source (e.g., battery or cell), a telemetry system (e.g., transceiver), one or more modules containing therapeutic circuitries (e.g., muscle stimulation, analgesic stimulation, performance feedback or RF ablation) coupled to the electrodes via an electrode switching circuit, and one or more sensors. The controller preferably comprises a processor, nonvolatile memory for storing firmware, implant identification information, and system and environmental data, and volatile memory that serves as a buffer for computations and instructions during execution and firmware updating. The controller preferably is coupled to battery, transceiver, electrode switching circuit, therapeutic module circuitries and sensors to monitor system status and to activate the various therapeutic module circuitries in accordance with the programming stored in the memory. The battery (or cell) can be a primary or secondary (rechargeable) configuration that preferably uses long-lasting lithium chemistry (e.g., lithium-ion or lithium polymer). If rechargeable, the battery is coupled to an inductive charging circuit, thereby enabling the battery to be periodically coupled to an external control system for charging. A radio frequency transceiver preferably is employed in the device for transmitting system information to, and receiving information from, the external control system, including system performance data, logged physiological data, commands, and firmware upgrades.

The stimulator system further comprises an external control system that may be coupled to the stimulator housing to supply power to the power source, to program/reprogram the controller, and to download system parameters and data stored within the memory. The external control system may be configured to transfer energy to the power source via inductive coupling. In a preferred embodiment, the external control system comprises a housing containing a controller, radio transceiver, inductive charging circuit and power source. The controller is coupled to the inductive charging circuit, power source, radio transceiver, and memory for storing information to be transmitted between the external control system and the implantable housing. The external control system may include a data port, such as a USB port or Bluetooth wireless connection, that permits the external control system to be coupled to a conventional computer, such as a personal computer or laptop computer, to configure the stimulation programs input to the stimulator and to review and analyze data received from the stimulator.

The stimulator system further may comprise monitoring and control software, configured to run on a conventional personal computer, laptop computer, "smart phone" or other computational device that enables the patient's physician to configure and monitor operation of the external control system and stimulator. The software may include routines for controlling any of a number of parameters associated with operation of the various therapeutic module circuitries incorporated in the stimulator. The software further may be configured, for example, to send immediate commands to the stimulator to start or stop muscle or analgesic stimulation, to perform RF ablation, or to take a current reading of muscle activity and adjust the stimulation regime(s), or to change the electrodes used to apply stimulation. Finally, the software may be configured to download data collected from the stimulator and stored on the external control system, such as during a patient visit to the physician's office.

Methods of operating the stimulator system of the present invention also are provided. The implantable portion of the stimulator may be placed subcutaneously using interventional radiologic techniques including radiographic imaging or ultrasound, while the electrode leads may be placed using surgical, percutaneous, or minimally invasive techniques. The stimulator preferably is programmed using radio frequency coupling of the transceivers in the stimulator and the external control system, while power is supplied to the battery of the stimulator by coupling the inductive charging circuits of the stimulator and external control system. Additional details of methods of implanting and operating a stimulator system in accordance with the present invention are described below.

V. BRIEF DESCRIPTION OF THE DRAWINGS

VI. DETAILED DESCRIPTION OF THE INVENTION

System Overview

Figure 1:
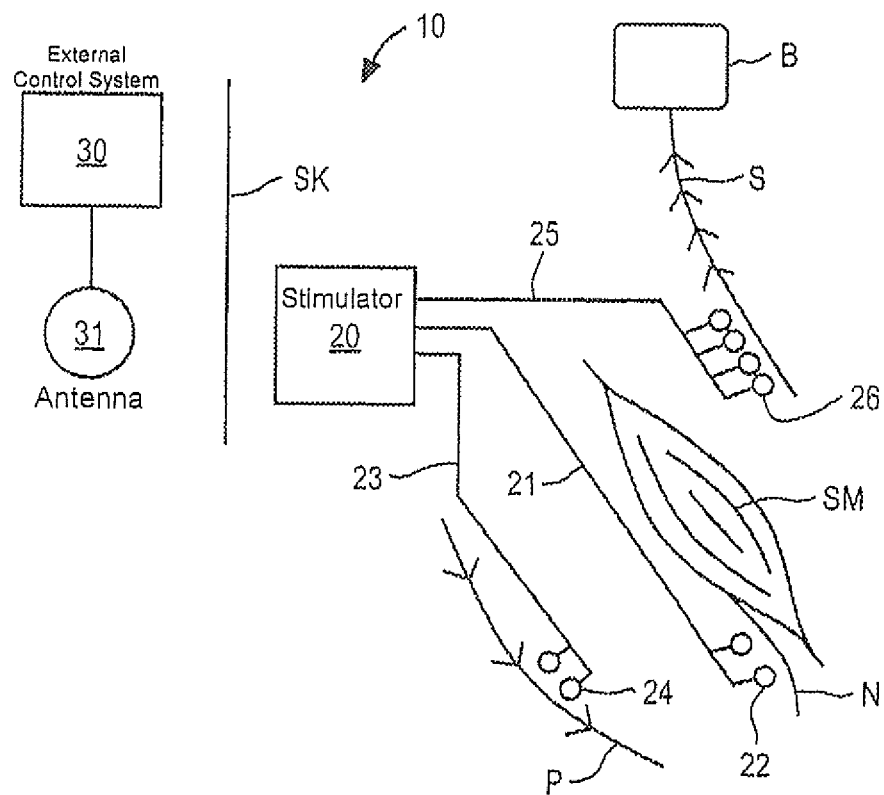
FIG. 1 is a schematic view of an exemplary embodiment of a stimulator system constructed in accordance with the principles of the present invention.

Referring to FIG. 1, an overview of an exemplary stimulator system constructed in accordance with the principles of the present invention is provided. In FIG. 1, components of the system are not depicted to scale on either a relative or absolute basis. Stimulator system 10 comprises implantable stimulator 20 and external control system 30. In the illustrated embodiment, software may be installed and run on a conventional laptop computer, and used by the patient's physician to program external control system 30 and/or to provide programming that is communicated by external control system 30 to stimulator 20. During patient visits, external system 30 may be coupled, either wirelessly or using a cable, to the physician's computer to download for review data stored on stimulator 20, or to adjust the operational parameters of the stimulator.

In FIG. 1 implantable stimulator 20 is connected to a plurality of electrode leads. Illustratively, electrode lead 21 is connected to electrode pair 22, which is situated close to or around a peripheral nerve N where the nerve enters skeletal muscle SM, which may be a multifidus muscle. Electrode pair 22 may deliver neuromuscular electrical stimulation ("NMES") pulses to nerve N that induce contraction of muscle SM to effect contraction of the muscle, and restoration of neural control and rehabilitation of the muscle, as described in the aforementioned U.S. Patent Application Publication No. US2008/0228241 to Sachs. Electrode lead 23 is illustratively disposed with electrode pair 24 adjacent or near to peripheral nerve P, such that electrical stimulation may be applied to achieve pain control in the region served by the peripheral nerves. Electrode lead 25 illustratively includes quadripolar electrode array 26, which is placed near spinal cord S in a manner well known to one skilled in the art to deliver Spinal Cord Stimulation therapy that reduces or blocks the transmission of pain signals to the patient's brain B.

Implantable stimulator 20 is controlled by, and optionally powered by, external control system 30, which communicates with stimulator 20 via antenna 31, which may comprise an inductive coil configured to transmit power and communicate information in a bidirectional manner across skin SK. The technology for antenna 31 is well known to one skilled in the art and may include a magnet, a coil of wire, a longer range telemetry system (such as using MICS), or technology similar to a pacemaker programmer. Alternatively, coil 30 may be used to transmit power only, and separate radio frequency transmitters may be provided in external control system 30 and stimulator 20 for establishing directional data communication.

Figure 2:
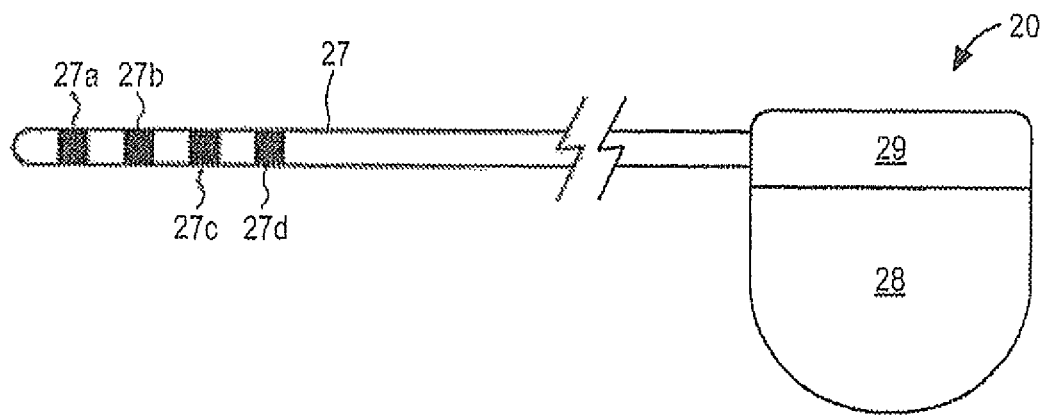
FIG. 2 is a side view of the implantable portion of the stimulator system of FIG. 1.

Referring now to FIG. 2, an exemplary embodiment of implantable stimulator 20 coupled to electrode lead 27 is described. As is common with other active implantable medical devices, the stimulator electronics are housed in a hermetically sealed metal housing 28. Housing 28 may comprise titanium or other biocompatible material, and includes connector block 29 that permits allows electrode lead 27 to be electrically coupled to the electronics within housing 28. While only one electrode lead 27 is shown coupled to connector block 29, it should be understood that multiple leads may connected to connector block 29, as shown in FIG. 1. Electrode lead 27 contains a plurality of electrodes 27a-27d that may be used for multiple purposes, as described in detail below. The construction of electrode lead, the electrode design and manufacture, and connector block 29 are all well known to those skilled in the art. As will also be understood by one of skill in the art, an electrode lead may contain more or fewer than four electrodes, as described in detail below with respect to FIGS. 8A and 8B.

Figure 3:
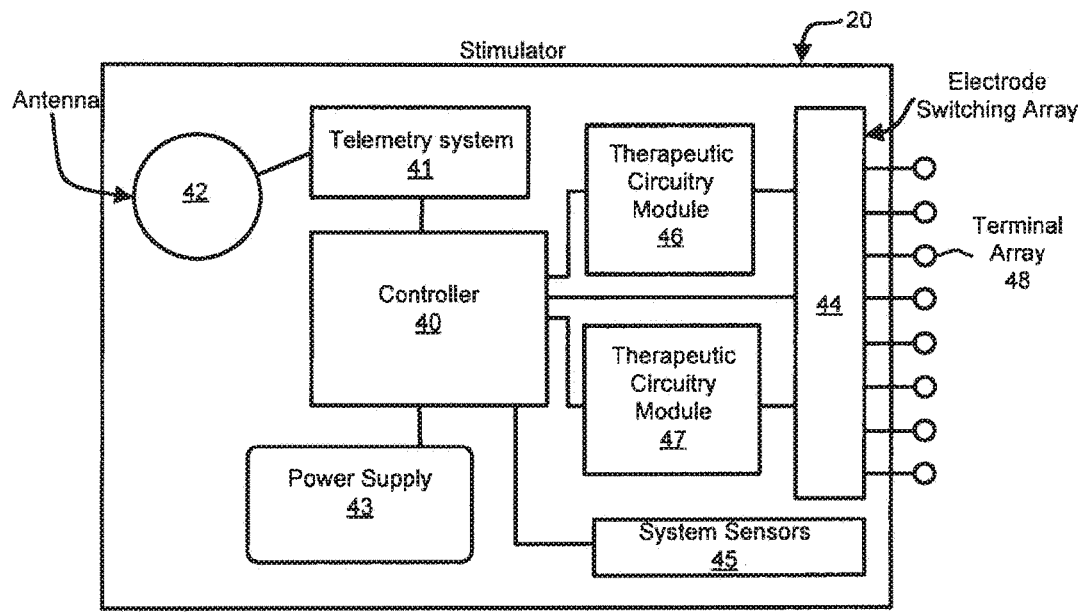
FIG. 3 is a generalized block diagram of the stimulator of FIG. 2.

With respect to FIG. 3, a generalized schematic diagram of the internal functional components of implantable stimulator 20 is now described. Stimulator 20 includes controller 40, telemetry system 41 coupled to antenna 42 (which may be inside or external to the hermetic housing), power supply 43, electrode switching array 44, system sensors 45, and therapeutic circuitry modules 46 and 47. Electrode switching array 44 is selectably coupled to terminal array 48, which is housed in connector block 29 and enables stimulator 20 to be coupled to one or more electrode leads, as shown in FIG. 1.

Controller 40 may comprise a commercially available microcontroller unit including a programmable microprocessor, volatile memory, nonvolatile memory such as EEPROM for storing programming, and nonvolatile storage, e.g., Flash memory, for storing a log of system operational parameters and patient data. Controller 40 is coupled to telemetry system 41 that permits transmission of energy and data between implantable stimulator 20 and external control system 30. Controller 40 also is coupled to therapeutic circuitry modules 46 and 47 that provide any of a number of complimentary therapeutic stimulation, analgesic, feedback or ablation treatment modalities as described in detail below. Controller 40 further may be coupled to electrode switching array 44 so that any set of electrodes of the electrode leads may be selectably coupled to therapeutic circuitry modules 46 and 47. In this way, an appropriate electrode set may be chosen from the entire selection of electrodes implanted in the patient's body to achieve a desired therapeutic effect. Electrode switching array 44 preferably operates at high speed, thereby allowing successive stimulation pulses to be applied to different electrode combinations.

Power supply 43 powers the electrical components of implantable stimulator 20, and may comprise a primary cell or battery, a secondary (rechargeable) cell or battery or a combination of both. Alternatively, power supply 43 may not include a cell or battery, but instead comprise a capacitor that stores energy transmitted through the skin via a Transcutaneous Energy Transmission System (TETs), e.g., by inductive coupling. Stimulator 20 may be programmed and/or controlled by, and may upload stored system and operational data to external control system 30 via telemetry system 41. In a preferred embodiment, power supply 43 comprises a lithium ion battery.

System sensors 45 may comprise one or more sensors that monitor operation of the systems of implantable stimulator 20, and log data relating to system operation as well as system faults, which may be stored in a log for later readout using the external control system. Sensors 45 may include, for example, a humidity sensor to measure moisture within housing 28, which may provide information relating to the state of the electronic components, or a temperature sensor, e.g., for measuring battery temperature during charging to ensure safe operation of the battery. System sensors 45 also may include a 3-axis accelerometer for determining whether the patient is active or asleep and to sense overall activity of the patient, which may be a surrogate measure for clinical parameters (e.g., more activity implies less pain), and/or a heart rate or breathing rate (minute ventilation) monitor, e.g., which may be obtained using one or more of the electrodes disposed on the electrode leads. Data from the system sensors may be logged by controller 40 and stored in nonvolatile memory for later transmission to external controller 30 via telemetry system 41.

If system sensor 45 includes an accelerometer, it may be used to determine the orientation of stimulator 20, and by inference the orientation of the patient, at any time. For example, after implantation, external control system 30 may be used to take a reading from the implant, e.g., when the patient is lying prone, to calibrate the orientation of the accelerometer. If the patient is instructed to lie prone during therapy delivery, then the accelerometer may be programmed to record the orientation of the patient during stimulation, thus providing information on patient compliance.

Implantable stimulator 20 illustratively includes two therapeutic circuitry modules 46 and 47, although more or fewer circuitry modules may be employed in a particular embodiment depending upon its intended application. As described in greater detail below with respect to further embodiments, therapeutic circuitry modules 46 and 47 may be configured to provide different types of stimulation, either to induce muscle contractions or to block pain signals in afferent nerve fibers, to monitor muscle contractions induced by stimulation and vary the applied stimulation regime as needed to obtain a desired result, or to selectively and intermittently ablate nerve fibers to control pain and thereby facilitate muscle rehabilitation As shown in FIG. 3, the therapeutic circuitry modules are coupled to and controlled by controller 40.

Typical stimulation parameters provided for different requirements are summarized below, and will be well known to those skilled in the art:

For neuromuscular electrical stimulation (NMES):
Bipolar electrode pairs
Biphasic rectangular charge balanced
0.5-500 ms pulse width (adjustable to control intensity)
10-30 Hz (to achieve tetanic contraction)
Constant current, <50 mA (<50V)
For PENS type stimulation:
Multiple bipolar electrode system
Biphasic pulses
20-40 Hz (including possibility of variable frequency over time of application of therapy)
Constant current (typically 5-20 mA)
For Spinal Cord Stimulation:
Multiple electrode configurations
Biphasic rectangular charge balanced
Typically 500 μsec pulse width
Current control (preferred) or voltage control, typically up to 10 mA into a 1 KΩ load
For Radio Frequency Ablation:
450-500 KHz
RF heating energy Embodiments comprising specific combinations of therapeutic circuitry modules in accordance with the principles of the present invention are described below.

Combination Stimulator for Neuromuscular Electrical Stimulation and Pain Relief

Figure 4:
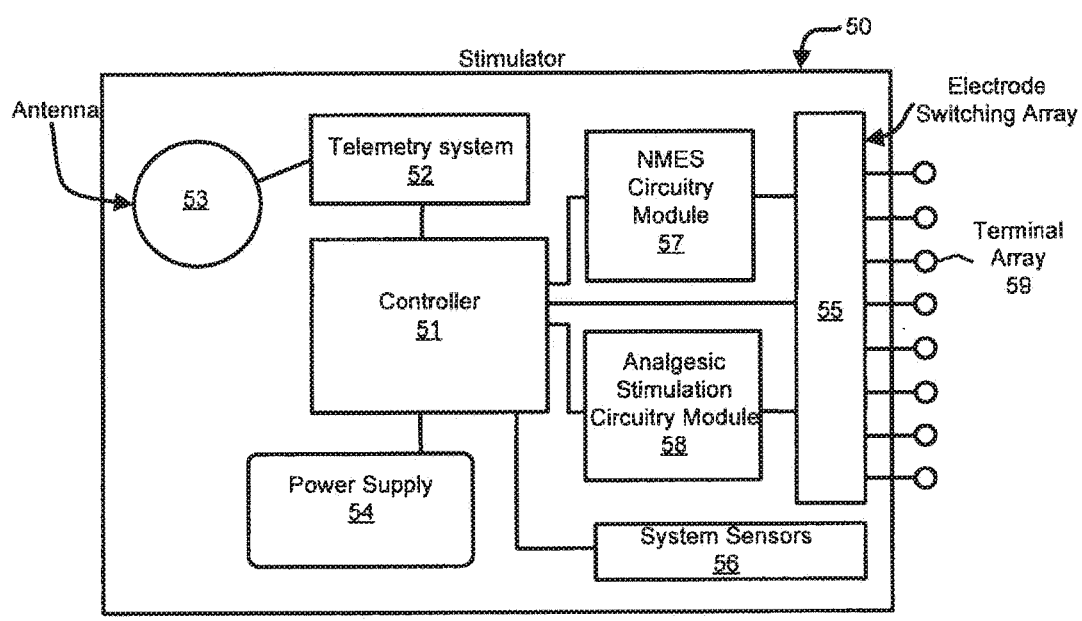
FIG. 4 is a schematic diagram of a first embodiment of the stimulator of FIG. 3, wherein the stimulator is configured to deliver both neuromuscular stimulation and analgesic stimulation to afferent nerve fibers.

Referring now to FIG. 4, a first embodiment of a neuromuscular electrical stimulation is described, which provides both stimulation to improve muscle tone and neural drive, while also providing stimulation to block or reduce transmission of pain along afferent nerve fibers. In the schematic of FIG. 4, implantable stimulator 50 includes controller 51, telemetry system 52 coupled to antenna 53, power supply 54, electrode switching array 55, system sensors 56, and NMES circuitry module 57 and analgesic stimulation circuitry module 58. Electrode switching array 55 is selectably coupled to terminal array 59, which is coupled to the connector block 29 (see FIG. 2) and enables stimulator 50 to be coupled to one or more electrode leads.

Each of components 51 to 59 operates in the manner described above for the embodiment of FIG. 3. More specifically, controller 51 preferably includes a programmable microprocessor, volatile memory, nonvolatile memory, and nonvolatile storage, and is coupled to and controls operation of telemetry system 52, NMES circuitry module 57, analgesic stimulation circuitry module 58, and electrode switching array 55. Power supply 54 powers the electrical components of implantable stimulator 50, and may comprise a primary cell or battery, a secondary cell or battery, a combination of both or neither. In the latter case, power supply 54 may comprise a capacitor that stores energy transmitted through the skin via TETS. Stimulator 50 may be programmed and/or controlled by, and may upload stored system and operational data to external control system 30 via telemetry system 52. System sensors 56 may comprise one or more sensors that monitor operation of stimulator 50, as well as patient parameters, such as movement, heart rate, etc., and may log data relating to these parameters for later readout using the external control system.

In the embodiment of FIG. 4, NMES circuitry module is configured to provide stimulatory pulses to the nerves innervating, or directly to the muscle fiber of, the multifidus or other selected muscle group to cause a predetermined series of muscle contractions in during a predetermined number of sessions to enhance muscle tone and improve neural drive in the muscle, as described in the above published application to Sachs, U.S. Patent Application Publication No. US 2008/0228241, the entirety of which is incorporated herein by reference.

Some patients receiving stimulator 50 may experience back pain due to previous injury and/or loss of muscle tone, while other patients may find the contractions induced by operation of the NMES circuitry to be unpleasant. Accordingly, stimulator 50 further includes analgesic stimulation circuitry module 58 to block or reduce pain associated with the previous injury or muscle contractions induced by the NMES therapy. As depicted in FIG. 1, in one preferred application of stimulator 50 (corresponding to stimulator 20 in FIG. 1), electrode pair 22 is situated on the medial branch of the dorsal ramus to deliver NMES pulses that cause muscle contraction to effect restoration of neural drive to and rehabilitation of the multifidus muscle. Analgesic stimulation circuitry module 58 may simultaneously be coupled to electrode pair 34, via electrode lead 23, and quad electrode 26, via electrode lead 25, to block or reduce pain signals generated in spinal cord S or peripheral nerve P. In addition, electrode pair 22 also may be used, e.g., by controller 51 switching electrode switching array 55 to couple electrode pair 22 to analgesic stimulation circuitry module 58, to deliver higher frequency stimulation to block afferent pain signals. In this manner, it is expected that NMES therapy may be provided while reducing patient discomfort and pain associated with any pre-existing injury.

Stimulator 50 and the electrodes also may be configured such that one set of electrodes is used to simulate the tissues on one side of the body, and another set of electrodes is used to simulate tissues on the other side of the body. In this manner, the stimulator and electrode system can be configured to deliver unilateral or bilateral stimulation, or a combination of electrodes stimulating tissues in no particular geometric arrangement.

Alternatively, a plurality of electrodes may be implanted on or adjacent to the medial branch of the dorsal ramus, such that one pair delivers NMES via circuitry module 57 to effect contraction of the multifidus muscle, and another pair simultaneously or successively delivers higher frequency stimulation via circuitry module 58 to block the pain signals in the afferent fibers. The pairs of electrodes may include one or more common electrodes. The timing of the different electrical stimulation delivered offers several options. For example, the pain blocking stimulation may occur simultaneously with the NMES stimulation, may be multiplexed with the NMES stimulation (i.e., time wise interleaved so that stimulation pulses are not delivered simultaneously on both electrode pairs), in an alternating manner (i.e., NMES then pain blocking and so on), or episodically, such as NMES for a period without pain blocking stimulation, and then pain blocking stimulation when the NMES is not being delivered.

In a preferred embodiment intended for clinical applications, NMES stimulation is applied to the multifidus in sessions, typically one hour per day over a period of a few weeks. Such a regime is similar to conventional strength training by physical exercise which typically follows a similar time course. In preparation for the sessions of NMES strength training, stimulator 50 may be used to apply SCS therapy to block or dampen the pain signals which may arise from the NMES exercise regime. In this way, the desired therapeutic effect of restoration of neural drive and rehabilitation of the multifidus may occur without substantial pain or discomfort. For patients afflicted with severe back or radicular pain, stimulator 50 offers the capability to apply SCS therapy at the same time as NMES rehabilitation therapy for the multifidus.

In one embodiment, the patient may have access to external control system 30, and can thus activate implantable stimulator 50 in accordance with a rehabilitation plan developed jointly with his or her physician. In this case, controller 51 may be programmed to provide a delay of specified duration between activation of the stimulator and initiation of the stimulation pulses. This delay allows the patient to assume a comfortable position before the stimulation is applied, e.g., by lying prone. The external control system also may include a multi-fimctional user interface, including a range of patient operated inputs (e.g., buttons, knobs, touch screen, etc.) that allows activation or suspension of different types of stimulation.

In another embodiment, implantable stimulator 50 may be programmed to ramp up and ramp down the strength and duration of the stimulation pulses. This can be done in at least one of two manners. In the first manner, the stimulation pulse intensity is increased gradually (e.g., over 0.5 to 1 second) to a programmed maximum value to elicit the desired muscle contraction and then ramped down slowly. In this way, the muscle contraction has a smooth on and off sensation for the patient. In the second manner, the therapeutic dose (i.e., the number of contractions of a therapy period) are programmed to increase gradually until the desired level is achieved and then decrease gradually to zero, in much the same way that a good muscle strength training regime provides a stretching or warm-up phase and cooldown phase. In this mode of operation, stimulator 50, via either input to the external control system or at a predetermined time, and following the stimulation delay (if any), ramps us the stimulation amplitude from a low level (e.g., beginning at zero) to a pre-determined maximum level over a pre-determined period of time. Likewise, upon conclusion of the stimulation therapy period, stimulator 50 ramps the amplitude down from the pro-determined maximum level to a low level. It is expected that this embodiment, which provides a gradual increase and decrease of stimulation intensity, will provide a more comfortable experience for some patients.

As discussed above, implantable stimulator 50 preferably contains nonvolatile memory for storage, and is programmed to log data during the therapy session, along with internal parameters of the device. Such data logging may also record data from system sensors 56, which may be downloaded from stimulator 50 using the external control system, to provide an indication of the effectiveness of the therapy. For example, if the sensors include a three axis accelerometer, then a patient's overall activity level on an hourly, daily, or weekly basis may be logged, for example, by recording an integral of all accelerometer measurements. The sensors also may include circuitry for determining heart rate, and such circuitry may be used to record the patient's maximum heart rate as a measure of overall activity.

In clinical use, the stimulator 50 is implanted subcutaneously, and system sensors 55 may be used to record and log baseline (i.e., pre-therapy) patient parameters such as total activity and maximum heart rate. The therapy then is enabled, and the data logging may be used to assess progress of the therapy and the patient's change in status. For example, if the accelerometer shows increased overall activity, this would indicate that the pain, which was previously inhibiting activity, had been ameliorated. Such data may be used by the physician to adjust the therapy by adjusting the programming of stimulator 50 using external control system 30, and/or such information may be provided to the patient as encouraging feedback.

Stimulator for Neuromuscular Stimulation with Performance Feedback

Figure 5:
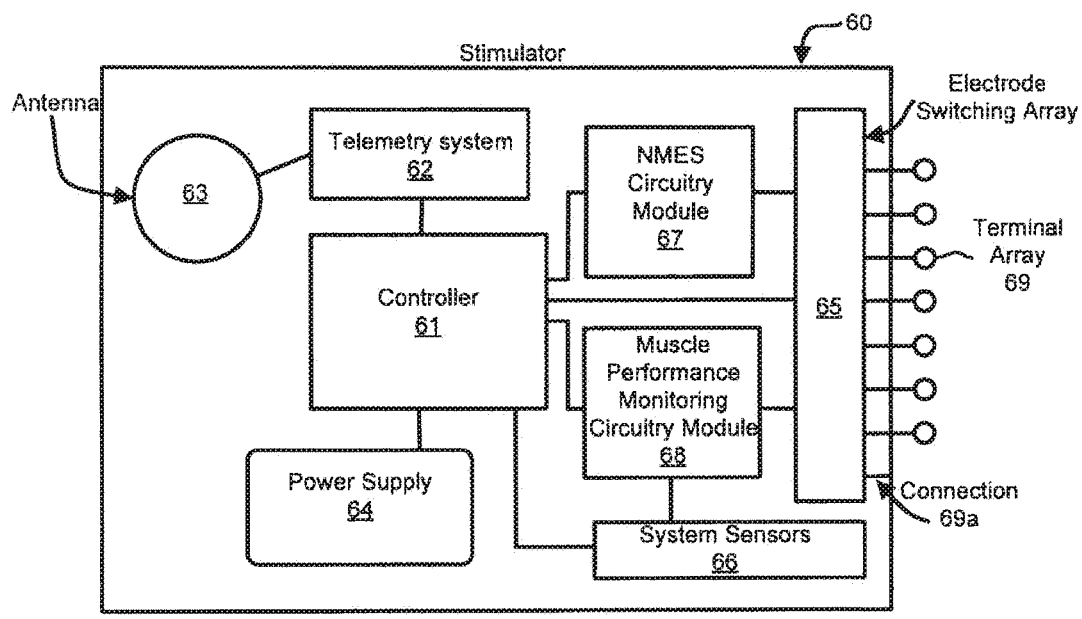
FIG. 5 is a schematic diagram of a second embodiment of the stimulator of FIG. 3 wherein the stimulator is configured to deliver neuromuscular stimulation, monitor the effects of the applied stimulation, and adapt the stimulation regime to improve muscle toning and reduce patient discomfort.

Referring now to FIG. 5, another embodiment of a stimulation system constructed in accordance with the principles of the present invention is described, in which the implantable stimulator provides a NMES stimulator therapy and further has the capability to monitor the progress of the therapy and to revise the therapy regime to reflect changes in the muscle characteristics resulting from the therapy. Such revision may be made by way of a physician periodically reprogramming the NMES parameters using external control system 30, or alternatively the NMES stimulation parameters may be adjusted dynamically and automatically modified to keep the muscle contraction at a certain predetermined efficacious and tolerable level. In some embodiments, stimulator 60 may provide a closed loop feedback system, in which the system instantaneously responds to physiological changes affecting the stimulation characteristics of the muscle.

Although a primary application of the inventive technology is to improve stability of the spine, it also may be advantageously applied in other areas of muscle rehabilitation, e.g.:

Restoration of function of leg muscles to allow standing and walking in paraplegic patients (referred to as Functional Electrical Stimulation (FES));

Rehabilitation of injured or weakened muscles following surgery or correction of osteoarthritis, such as rehabilitation of the quadriceps after knee surgery;

Restoration of neural drive and rehabilitation of muscles that are part of the stabilizing system in the back, including the lumbar multifidus;

Providing stimulation to effect breathing (diaphragm and/ or intercostal muscles); and Providing mechanical muscle power to perform a bodily function, for example, as in cardiomyoplasty.

The implantable NMES stimulator described in the above-incorporated Sachs application discusses that the parameters for electrical stimulation may be programmed into the stimulator following testing by the physician of stimulation thresholds. Therapy parameters such as duration, frequency and strength of contraction also may be programmed into the stimulator according to the patient's needs, and the stage of therapy delivery. In some cases it is expected that the programmed parameters may need to be changed, for example during the course of the therapy program as the muscle becomes rehabilitated.

Stimulator 60 of FIG. 5 is designed to improve the NMES performance and reduce the need for frequent reprogramming by monitoring muscle performance during therapy, and adjusting the stimulation parameters accordingly. More specifically, implantable stimulator 60 includes controller 61, telemetry system 62 coupled to antenna 63, power supply 64, electrode switching array 65, system sensors 66, and NMES circuitry module 67 and muscle performance monitoring circuitry module 68. Electrode switching array 65 is selectably coupled to terminal array 69, which is coupled to the connector block 29 (see FIG. 2) and enables stimulator 60 to be coupled to one or more electrode leads. Electrode switching array 65 also may include connection 69a to the housing of stimulator 60, so that the housing functions as an electrode.

Each of components 61 to 67 and 69 operates in the manner described above for the embodiment of FIG. 3. Controller 61 preferably includes a programmable microprocessor, volatile memory, nonvolatile memory, and nonvolatile storage, and is coupled to and controls operation of telemetry system 62, NMES circuitry module 67, muscle performance monitoring circuitry module 68, and electrode switching array 65. Power supply 64 powers the electrical components of implantable stimulator 60, and may comprise a primary cell or battery, a secondary cell or battery, a combination of both or neither. In the latter case, power supply 64 may comprise or include a capacitor that stores energy transmitted through the skin via a Transcutaneous Energy Transmission System ("TETS"). Stimulator 60 may be programmed and/or controlled by, and may upload stored system and operational data to external control system 30 via telemetry system 62. System sensors 66 may comprise one or more sensors that monitor operation of stimulator 60, as well as patient parameters, such as movement, heart rate, etc., and may log data relating to these parameters for later readout using the external control system.

In accordance with one aspect of the present invention, stimulator 60 further comprises muscle performance monitoring circuitry module 68 coupled to controller, and designed to monitor one or more parameters of muscle performance. The measured parameters may be used to automatically modify the therapy delivered by NMES circuitry module 67, and/or to provide stored and telemetered information via telemetry system 62 and external control system 30 that enable the physician to modify the parameters. In one preferred embodiment, muscle performance monitoring circuitry module 68 may be coupled through electrode switching array 65 to selected electrodes coupled to terminal array 69 to measure electrical parameters of the tissue, such as impedance, or evoked potential from the stimulation. Circuitry module 68 may in addition be coupled to system sensor 66, for example, to obtain data from an accelerometer or other movement transducer, and/or temperature or pressure. Circuitry module 68 also may be configured to receive inputs from other types of body sensors such as are known in the art, including those monitoring chemical properties (e.g., pH sensor, etc.).

Circuitry module 68 preferably includes at least one listening amplifier configured for electromyography (EMG). EMG is an electrical signal produced by muscle when it contracts, and the strength (power) of the EMG is an indicator of strength of muscle contraction. Configuration of an amplifier for measurement of EMG, e.g., gain, frequency response, impedance, etc., is well known to those skilled in the art. As described in Stokes, Ian A F, Sharon M Henry, and Richard M Single, "Surface EMG electrodes do not accurately record from lumbar multifidus muscles." Clinical Biomechanics (Bristol, Avon) 18, no. 1 (January 2003): 9-13, it is known that certain muscles, such as the deep fibers of the lumbar multifidus, surface EMG provides an unreliable signal. Accordingly, the implantable electrode leads used with stimulator 60 advantageously are expected to provide a useful EMG signal.

In another embodiment, circuitry modules 67 and 68 may be configured to perform impedance measurements, in a manner similar to that described in U.S. Pat. No. 6,406,421 B1 to Grandjean et al. As is well known, an electrical impedance measurement may be performed by injecting a current through one pair of electrodes, and measuring voltage through a different pair of electrodes disposed approximately along the same geometric path. See, e.g., Rutkove, S. B., "Electrical impedance myography: Background, current state, and future directions", Muscle & Nerve 40, No. 6 (December 2009): 936-46. In one implementation, a first pair of electrodes consisting of the stimulator housing (via connection 69a) and one or more of electrodes disposed on an electrode lead may be used to inject current into the tissue (e.g., from NMES circuitry module 67), while voltage is measured by circuitry module between the stimulator housing and a different set of one or more of electrodes on the electrode leads. Alternatively, the same set of electrodes (including the stimulator housing) may be used for both injecting current and measuring the resulting voltage.

The foregoing impedance measurements may be of direct current (DC) or alternating current (AC). With AC impedance measurement, additional useful information may be obtained such as phase, frequency spectrum, and changes in parameters. The electrical impedance so measured is an indication of the tissue volume and tissue organization (anisotropy) between the measurement electrodes, as reported in Ganrmirian et al., "Discriminating neurogenic from myopathic disease via measurement of muscle anisotropy", Muscle Nerve, 2009 January; 39 (1): 16-24. See also, Miyatani, M., et al., "Validity of estimating limb muscle volume by bioelectrical impedance", J. Applied Physio. (Bethesda, Md. 1985) 91, no. 1 (July 2001): 386-94. Accordingly, judicious placement of the electrodes and the stimulator housing will ensure that only the tissue of interest (e.g., the target muscle) is in the path of the injected and measured voltage. As a muscle contracts, its dimensions change, and this will generate a change in electrical impedance. Thus, measurement of electrical impedance may be used as a surrogate measure of muscle contraction.

In another embodiment, circuitry module 68 may include or be coupled to a transducer that senses mechanical motion, such as vibration, acceleration or deflection, and may include piezoelectric polymers (e.g., PVDF) placed on a lead. The signal from such a transducer provides a surrogate measure of muscle contraction. In a further alternative embodiment, circuitry module 68 may include or be coupled to a transducer that senses pressure, such as a MEMS pressure sensors disposed on a lead, and which thus provides a surrogate measure of muscle contraction.

In yet another embodiment, stimulator 60 is configured to sense EMG from more than one muscle, using multiple electrode leads or multiple electrodes on a single lead that passes through more than one muscle. In this case, the listening amplifier of circuitry module 68 is multiplexed to listen for EMGs from more than one muscle. Alternatively, circuitry module 68 may include multiple listening amplifiers that are arranged to simultaneously listen to EMGs from more than one muscle. It is well-known, for example from Jaap van Dieen et al., "Trunk Muscle Recruitment Patterns," Spine Vol. 28, Number 8 pg 834-841, that the relative timing and amplitude of EMGs in trunk muscles during the performance of specific tasks is different between healthy individuals and patients experiencing low back pain due to spinal instability. In patients with spinal instability, recruitment patterns of the trunk muscles may be altered to compensate for the lack of spinal stability. The amplitude and timing of EMGs measured from multiple trunk muscles therefore may be used to diagnose the presence and degree of spinal instability, as well as the change of spinal instability during a course of therapy. The EMG data may be used to automatically modify treatment parameters, or such data may be stored for later review by the physician to assist in diagnosis and revision of the therapy parameters.

In the embodiment of FIG. 5, muscle performance monitoring circuitry module 68 is configured to measure muscle contraction induced by NMES circuitry module 67, and to modify the therapeutic parameters as muscle performance changes. In particular, the initial therapeutic parameters, such as dose and duration of therapy session, are established and programmed into stimulator 60 using external control system 30. Between therapy sessions, muscle performance may be monitored continuously or periodically using circuitry module 68. When the change in measured muscle performance exceeds a predetermined physician selected threshold, circuitry module 68 may instruct controller 61 to modify the parameters for subsequent NMES therapy sessions. For example, if the monitoring parameters reveal that the muscle mass has increased, indicative of muscle rehabilitation, or contractility has decreased, then the therapy dose may be automatically reduced some pre-determined amount as previously programmed by the physician.

In an alternative embodiment, muscle performance may be used to inhibit muscle contraction. For example, in certain types of low back pain, pain is caused by spasm of certain muscles in the back. Such spasm is accompanied by continuous increase in EMG activity. In accordance with one aspect of the present invention, NMES stimulation may be used to inhibit muscle contraction by configuring the listening amplifier of circuitry module 68 to continuously or periodically measure EMG. If the EMG satisfies conditions indicating that muscle spasm has occurred, then NMES circuitry module is directed by controller 61 to apply stimulation to the nerve innervating the muscle in spasm to block conduction of signals from the nervous system which cause the muscle spasm, thereby preventing spasm. The stimulation provided by NMES circuitry module may be inhibited from time to time to allow circuitry module 68 to assess from the EMG signal if the muscle is still in spasm; if spasm has ceased, then application stimulation by NMES circuitry module 67 is terminated.

In an alternative embodiment, muscle performance monitoring circuitry module 68 may be configured to measure a combination of EMG and tissue impedance to confirm that a muscle is in spasm, thereby improving the safety and reliability of the measurement. Muscle performance monitoring circuitry module 68 also may be used to track changes in activity and health of the muscle in response to neural activity. In other words, the amount of muscle contraction as determined by impedance measurement of tissue volume may be correlated to the amount of electrical activity in the muscle as determined by EMG. Further still, the electrodes and muscle performance monitoring circuitry module 68 may be configured to record electrical signals from the nerves as well as the muscle, such that a measurement of the EMG (and/or tissue volume) in response to neural activity may be used as an indication of the health of the muscle.

Muscle performance monitoring circuitry module 68 also may employ measurement of the change in muscle mass in response to NMES of the nerve to adjust the electrical stimulation parameters. In this case, an empirically derived transfer function may be determined that relates electrical stimulation parameters, such as current, pulse width, frequency and duration, to the strength of contraction of the muscle. Over time, this transfer function may change, for example, as a result of electrode changes from movement or tissue ingrowth. Thus, the strength of muscle contraction may be used to automatically adjust the electrical parameters of the NMES stimulation provided by circuitry module 67 to achieve a desired muscle contraction.

Stimulator with RF Ablation Capability

Figure 6:
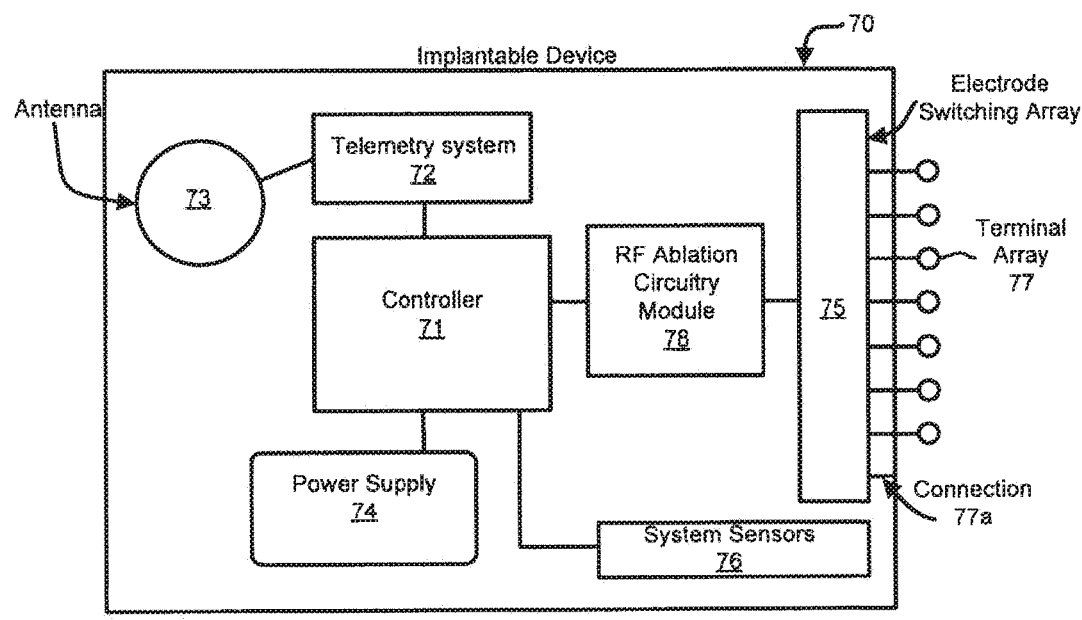
FIG. 6 is a schematic diagram of an alternative embodiment of the apparatus of the present invention that provides a selective ablation capability.

Referring to FIG. 6, in accordance with another aspect of the present invention, an implantable RF ablation device is described. Although a primary application of the inventive technology is pain reduction in connection with improving stability of the spine, the inventive technology may be advantageously applied in other areas, for example:

RF rhizotomy, in which a sensory nerve is ablated to prevent sensory signals (e.g., pain) from reaching the brain, such as rhizotomy of the medial branch of the dorsal ramus in patients with facet joint pain;

RF ablation of unresectable tumors located in the liver, brain, musculoskeletal system, thyroid and parathyroid glands, pancreas, kidney, lung, and breast, in which it is difficult to achieve complete tumor necrosis, leading to recurrence of the tumors and necessitating repeated RF ablation; and Treatment of tumors in which the root of the tumor is located in tissue that is considered too risky for surgical intervention, such as tumors with roots in the digestive tract, uterine wall or certain oesophageal tumors, and for which regular repeat surgery is required to remove new growths.

The field of RF ablation is well developed, and parameters suitable for ablating nerve fibers and other tissues, such as RF energy, and attendant issues is well known to those of ordinary skill in the art. See, e.g., Gazelle et al., "Tumor ablation with radio-frequency energy", Radiology, December 2000: 217(3): 633-46 and Haemerrich et at, "Thermal tumour ablation: devices, clinical applications and future directions", Int. Hyperthermia, 2005 December; 21(8):755-60. To the inventors' knowledge, however, no one has suggested an RF ablation device that is configured to be chronically implanted and capable of performing repeated RF ablation.

Referring now to FIG. 6, implantable device 70 is described, which is intended for chronic implantation to perform serial RF ablations in scenarios where it is necessary to repeat RF ablation of tissue in a particular region of the body after certain periods of time. The components of device 70 correspond closely to those described above with respect to the embodiment of FIG. 3, and includes controller 71, telemetry system 72 coupled to antenna 73, power supply 74, electrode switching array 75, system sensors 76, and terminal array 77. As in the preceding embodiments, electrode switching array 75 is selectably coupled to terminal array 77, which is coupled to the connector block 29 (see FIG. 2) that accepts one or more implantable electrode leads. Electrode switching array 75 also may include connection 77a to the housing of device 70, so that the housing functions as an electrode. In accordance with this aspect of the present invention, device 70 further comprises RF ablation circuitry module 78, as further described below.

Each of components 71 to 77 operates in the manner described above for the embodiment of FIG. 3. Controller 71 preferably includes a programmable microprocessor, volatile memory, nonvolatile memory, and nonvolatile storage, and is coupled to and controls operation of telemetry system 72, electrode switching array 75 and RF ablation circuitry module 78. Power supply 74 powers the electrical components of device 70, and may comprise a primary cell or battery, a secondary cell or battery, a combination of both, or neither. In the latter case, power supply 74 may comprise or include a capacitor (such as a super capacitor of technology known to those skilled in the art) that stores energy transmitted through the skin via TETS. Device 70 may be programmed and/or controlled by, and may upload stored system and operational data to external control system 30 via telemetry system 72. System sensors 76 may comprise one or more sensors that monitor operation of device 70, as well as patient parameters, such as tissue impedance, and may log data relating to these parameters for later readout using the external control system.

In accordance with this aspect of the present invention, device 70 further comprises RF ablation circuitry module 78 coupled to controller, and designed to periodically ablate tissue or nerve fibers using RF energy. Accordingly, controller 71 may be configured to control operation of the telemetry system 72 to receive energy wirelessly from external control system 30 and store that energy in power supply 74, and may be configured to communicate the amplitude of received power back to the external control system via telemetry system 72 or via modulation of the impedance of the antenna 73. To ensure that RF ablation is only carried out at the direction of the external control system, device 70 may not include battery or capacitor, but instead may be arranged so that it is energized only when in communication with the external control system.

Expected energy requirements for the RF ablation circuitry module are in a range of about 1-40 watts, depending upon the intended application. TETS systems with this power capacity are well known to those skilled in the art and have been used, for example, with artificial hearts or Left Ventricular Assist Devices (LVADs). However, the physical volume and other requirements of a high power TETS system may preclude its use in applications where the available surgical locations are limited. Thus, in an alternative embodiment, the TETS system may be of lower power capacity than the requirements of the RF generator, and device 70 may include an energy storage element, such as a super capacitor or low impedance secondary (rechargeable) cell, for powering RF ablation circuitry module 78. In use, the TETS may operate continuously, such that a signal is generated when there is adequate energy stored in the implantable device to deliver the RF ablation energy at the desired power and for the desired time. As an example, a TETS system capable of transferring 1 W may be used to supply RF energy delivery of 5 W with 20% duty cycle.

In this embodiment, telemetry system 72 enables communications between the external control system and device 70, allowing the implantable device to receive device and RF ablation operating parameters, as well as communicate logged information such as impedance between electrodes, temperature data and battery status to the external control system. Telemetry system 71 also may provide programming to controller 71 to reconfigure the operative electrodes through which ablation energy is supplied using electrode switching array 75, thereby allowing any electrode of a plurality of electrodes to be configured as a cathode, an anode or unconnected. The housing of device 70 also may be configured as an electrode via connection 77a of terminal array 77. The foregoing capabilities provide flexibility in the location of ablation lesions and allow the physician to compensate for electrode movement after implantation.

System sensors 76 advantageously may be used to monitor the temperature of the tissue near the electrodes thru which energy for ablation is delivered. Typical tissue temperatures for RF ablation range from 50 C to 130 C, depending on the type of tissue being ablated and the time allocated to the ablation. System sensors 76 may comprise, e.g., temperature sensors disposed within the device housing, or alternatively may measure the temperature of the connection to the electrode leads, and use that data to infer or predict the tissue temperature. Temperature sensors may also be incorporated into the leads and placed closer to the tissue targeted for ablation. System sensors 76 may be used in a passive (measuring) mode, or alternatively may comprise part of a feedback control system that continually or intermittently adjusts power delivered by the RF ablation circuitry module so that the temperature of the ablated tissue is maintained between desired limits for safety and efficacy.

Figure 7:
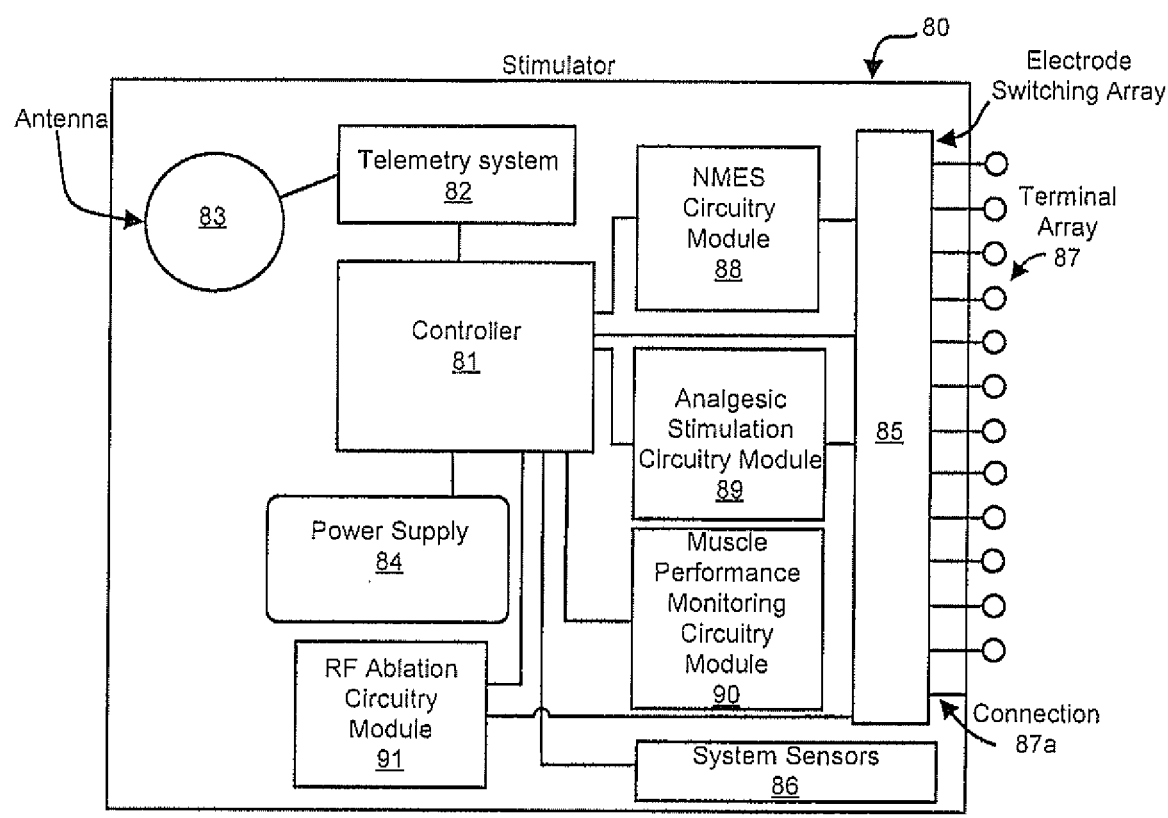
FIG. 7 is a schematic diagram of a further alternative embodiment of the stimulator of the present invention that includes neuromuscular stimulation, pain reduction, performance feedback and selective nerve ablation capabilities.

Referring now to FIG. 7, an implantable stimulator illustratively incorporating all of the therapeutic circuitry modules described for the preceding embodiments is described. Implantable stimulator 80 corresponds to stimulator 20 of FIG. 1, and is programmed and controlled and/or powered by external control system 30. Stimulator 80 is intended for use, for example, in a stimulator that provides NMES stimulation, analgesic stimulation to block or reduce afferent pain signals in a nerve, and permits periodic nerve ablation (such as rhizotomy). Further in accordance with this aspect of the present invention, stimulator 80 includes muscle performance monitoring circuitry that supports testing of nerve fibers prior to rhizotomy, which to guide proper selection of the ablation electrodes.

Stimulator 80 of FIG. 7 includes controller 81, telemetry system 82 coupled to antenna 83, power supply 84, electrode switching array 85, system sensors 86, terminal array 87, NMES circuitry module 88, analgesic stimulation circuitry module 89, muscle performance monitoring circuitry module 90, and RF ablation circuitry module 91. As in the preceding embodiments, electrode switching array 85 is selectably coupled to terminal array 87 under the control of controller 81, and enables any one or more of the therapeutic circuitry modules of stimulator 80 to be selectably coupled to selected electrodes of one or more electrode leads. Electrode switching array 85 also may include connection 87a to the housing of stimulator 80, so that the housing also may serve as an electrode.

Each of components 81 to 87 operates in the manner described above for the embodiment of FIG. 3. Controller 81 preferably includes a programmable microprocessor, volatile memory, nonvolatile memory, and nonvolatile storage, and is coupled to and controls operation of telemetry system 82, electrode switching array 85, NMES circuitry module 88, analgesic stimulation circuitry module 89, muscle performance monitoring circuitry module 90, and RF ablation circuitry module 91. Power supply 84 powers the electrical components of implantable stimulator 80, and may comprise a primary cell or battery, a secondary cell or battery, a combination of both, or neither, as discussed above. Stimulator 80 may be programmed and/or controlled by, and may upload stored system and operational data to external control system 30 via telemetry system 82. System sensors 86 may comprise one or more sensors that monitor operation of stimulator 80, as well as various patient parameters as discussed above.

In accordance with this aspect of the present invention, stimulator 80 further comprises NMES circuitry module 88 and analgesic stimulation circuitry module 89, as described above with respect to the embodiment of FIG. 4, muscle performance monitoring circuitry module 90 as described above with respect to the embodiment of FIG. 5, and RF ablation circuitry module 91 as described above with respect to the embodiment of FIG. 6. In this manner, a patient in need of spinal muscle rehabilitation and restoration of neural drive may have the full range of therapeutic modalities available. In particular, stimulator 80 as initially implanted by the physician, may be programmed to provide NMES stimulation and stimulation to block pain signals in afferent nerves. As muscle strength and contractility improve over the course of the therapy, the muscle performance monitoring circuitry module 90 may measure the progress of the therapy and adjust the NMES stimulation parameters or circumvent spasm. In addition, depending upon the patient's reported condition and measurement data provided by the muscle performance monitoring circuitry module 90, the physician may periodically activate RF ablation circuitry module 91 to denervate selected nerve fibers.

Electrode Lead Systems

Figure 8A:
FIGS. 8A and 8B are, respectively, a plan view and detailed view of an exemplary electrode constructed in accordance with the principles of the present invention.
Figure 8B:
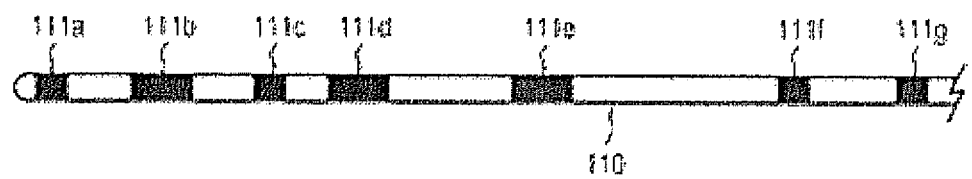

In view of the capabilities of the various implantable stimulators described herein, it may be advantageous to provide an electrode lead specially configured for use with such stimulators. Referring to FIGS. 8A and 8B, electrode leads configured to provide NMES stimulation to a nerve to cause muscle contraction; to stimulate a nerve to inhibit pain signals from propagating to the brain; to stimulate a nerve to inhibit motor nerve signals thereby reducing or stopping contraction of a muscle (e.g., in spasm); to record electrical signals such as electromyography or tissue impedance; or for performing in situ RF ablation are now described.

With respect to FIG. 8A, electrode lead 100 carrying electrodes 101a to 101f is described. The number of electrodes may be as few as 1 and as many as may be realistically placed within the target anatomical space. Electrode configurations commonly used in the art include 1 (for unipolar stimulation), 2, 4 (peripheral nerve stimulation), 8, 16 (spinal cord stimulators) or up to 22 electrodes (cochlear implants). For the purpose of this disclosure, distal-most electrode 101a will be referred to as electrode #1, electrode 101b will be electrode #2 and so on moving proximally along lead 100 up to the total number of electrodes.

When employed with an implantable stimulator as described herein that provides multiple independent current outputs, electrode lead 100 is capable of delivering multiple therapies simultaneously, in an overlaid fashion or staggered. Electrodes 101a to 101f may be sized and positioned relative to each other to allow for generation of a voltage field tailored to the specific type of stimulation, sensing or ablation desired for the given therapies.

In one embodiment, electrode lead 100 is placed parallel to a target nerve in a caudal to cranial orientation (with the cranial direction being the direction tending towards afferent neural activity). Then so positioned, electrodes 1 and 2, which are most cranial, may be sized and spaced to allow for optimal blocking of afferent pain signals being transmitted along the nerve (for example the pain signals being carried from the facet joint along the medial branch). More caudally, electrodes 3 and 4 may be sized and spaced to allow for optimal recruitment of large fiber motor neurons. Because the action potentials required for activation of a muscle travel efferently, these potentials are not blocked by the more cranial blocking action of electrodes 1 and 2. Finally, electrodes 5 and 6, placed most caudally, may be sized and positioned for sensing and recording of muscle recruitment through capturing the EMG signal of the muscle, which may be processed, for example, by the muscle performance monitoring circuitry module as described above with respect to the embodiment of FIG. 4. Such an arrangement therefore allows for simultaneous blocking of pain arising from the facet joint, stimulation of the motor fibers of the nerve eliciting muscle contraction, and sensing of the elicited response (which would enable a closed loop system, improving device longevity and recruitment efficiency) without any of the stimulation pulses negatively impacting the performance of the others.

With respect to FIG. 8B, alternative electrode lead 110 carrying electrodes 111a to 111g is described. Distal-most electrode 111a again will be referred to as electrode #1, electrode 111b will be electrode #2 and so on moving proximally along lead 111. In the embodiment of FIG. 8B, a blocking action of electrodes 1 and 2 may be used to mute the sensory perception of stimulation. In this manner, NMES stimulation therapy of the motor fibers in patients may be achieved where the patients would otherwise not tolerate the stimulation because of the resulting bi-directional action potential generated by neural stimulation. It also may be possible to use electrodes 5 and 6, which will likely be placed intramuscularly, to record the volume EMG signal in the muscle. Changes in this signal over time may provide an indication of the degree to which motor control has been compromised due to injury. When such data are compared over time during the period after a therapy regime has been completed, the data may be used as a positive indicator that additional therapy may be required to maintain spinal stability.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A method to alleviate back pain, the method comprising:
    placing at least two electrodes comprising a first electrode and a second electrode within a lower back of a human such that the first and second electrodes are implanted adjacent to tissue associated with at least one muscle supporting stability of the human's spine;
    electrically stimulating, via the first electrode, efferent nervous tissue associated with the at least one muscle to cause contraction of the at least one muscle to facilitate rehabilitation; and
    electrically stimulating, via the second electrode, afferent nervous tissue associated with the at least one muscle to block pain signals resulting from electrically stimulating the efferent nervous tissue.

2. The method of claim 1, wherein placing the at least two electrodes comprises placing the first electrode adjacent to a medial branch of a dorsal ramus nerve, and
    wherein electrically stimulating, via the first electrode, the efferent nervous tissue comprises electrically stimulating the medial branch of the dorsal ramus nerve to cause contraction of a multifidus muscle.

3. The method of claim 1, wherein placing the at least two electrodes comprises placing the second electrode adjacent to a peripheral nerve, and
    wherein electrically stimulating, via the second electrode, the afferent nervous tissue comprises electrically stimulating the peripheral nerve to block the pain signals traveling towards the human's brain from the human's spinal cord.

4. The method of claim 1, wherein electrically stimulating, via the first electrode, the efferent nervous tissue improves muscle tone and neural drive.

5. The method of claim 1, wherein electrically stimulating, via the first electrode, the efferent nervous tissue causes a predetermined series of muscle contractions during a predetermined number of sessions.

6. The method of claim 5, wherein the predetermined number of sessions comprises one hour per day over a period of weeks.

7. The method of claim 1, wherein electrically stimulating, via the first electrode, comprises electrically stimulating at a stimulation rate between 10-30 Hz.

8. The method of claim 1, wherein electrically stimulating, via the first electrode, comprises increasing a stimulation pulse intensity of the electrical stimulation to a predetermined maximum value to elicit a desired muscle contraction, and ramping down the electrical stimulation applied via the first electrode.

9. The method of claim 1, wherein electrically stimulating, via the first electrode, comprises increasing a therapeutic dose of the electrical stimulation until a desired level is achieved, and decreasing the therapeutic dose of the electrical stimulation to zero.

10. The method of claim 9, wherein the therapeutic dose comprises a number of muscle contractions within a therapy period.

11. The method of claim 1, wherein electrically stimulating, via the second electrode, comprises electrically stimulating at a higher stimulation frequency than electrically stimulating via the first electrode.

12. The method of claim 1, wherein electrically stimulating via the first and second electrodes comprises simultaneously electrically stimulating via the first and second electrodes.

13. The method of claim 1, wherein electrically stimulating via the first and second electrodes comprises electrically stimulating via the first and second electrodes in a time-wise interleaved manner.

14. The method of claim 1, further comprising:
adjusting parameters for electrical stimulation; and
electrically stimulating, via the first or second electrode, at the adjusted parameters.

15. The method of claim 1, wherein placing the at least two electrodes comprises placing a lead having the at least two electrodes disposed thereon within the lower back of the human.

16. The method of claim 1, wherein placing the at least two electrodes comprises placing a first lead having the first electrode disposed thereon and a second lead having the second electrode disposed thereon within the lower back of the human.

17. The method of claim 1, further comprising electrically coupling the at least two electrodes to a pulse generator, wherein electrical stimulation via the first and second electrodes is based on an electrical stimulation regime programmed in the pulse generator.

18. The method of claim 17, wherein the pulse generator comprises a first circuitry module operatively coupled to the first electrode and a second circuitry module operatively coupled to the second electrode,
wherein electrically stimulating, via the first electrode, the efferent nervous tissue comprises electrically stimulating based on programming associated with the first circuitry module, and
wherein electrically stimulating, via the second electrode, the afferent nervous tissue comprises electrically stimulating based on programming associated with the second circuitry module.

19. The method of claim 17, further comprising implanting the pulse generator.

20. The method of claim 19, further comprising transmitting data associated with the pulse generator from the pulse generator to an external control system.

21. The method of claim 20, further comprising receiving power at the pulse generator from the external control system to charge a battery of the pulse generator.

22. The method of claim 20, further comprising transmitting data associated with the pulse generator from the pulse generator to a computer running monitoring and control software.

* * * * *